| United States Patent [19] | [11] Patent Number: 4,707,492 |
| Myers-Keith | [45] Date of Patent: Nov. 17, 1987 |

[54] METHOD FOR INCREASING FERTILITY IN ANIMALS BY CONTROLLING AND STIMULATING OVULATION

[75] Inventor: Paula Myers-Keith, West Terre Haute, Ind.

[73] Assignee: International Minerals & Chemical Corp., Terre Haute, Ind.

[21] Appl. No.: 859,359

[22] Filed: May 5, 1986

[51] Int. Cl.⁴ .......................................... A61K 31/335
[52] U.S. Cl. .................................................... 514/450
[58] Field of Search ........................ 514/450; 549/268

[56] References Cited

U.S. PATENT DOCUMENTS

| 3,428,526 | 2/1969 | Sigg et al. | 195/80 |
| 3,463,860 | 8/1969 | Strandskov et al. | 424/308 |
| 3,565,991 | 2/1971 | Short | 424/243 |
| 4,228,079 | 10/1980 | Calton | 549/268 |
| 4,283,419 | 8/1981 | Voronkov et al. | 424/316 |
| 4,491,593 | 1/1985 | Gallegos | 424/317 |

OTHER PUBLICATIONS

Chemical Abstracts, 48:5832d, 1954 (Delmotte et al.).
Merck Index, 9th ed., 1976, p. 811.

*Primary Examiner*—Leonard Schenkman
*Attorney, Agent, or Firm*—W. R. Guffey; T. L. Farquer

[57] ABSTRACT

Monorden is administered to animals to increase fertility by inducing multiple births, promoting estrus synchronization, increasing litter sizes, and increasing conception rates.

16 Claims, No Drawings

4,707,492

METHOD FOR INCREASING FERTILITY IN ANIMALS BY CONTROLLING AND STIMULATING OVULATION

This invention relates generally to methods for increasing fertility in animals by controlling and stimulating ovulation and particularly to a method for increasing fertility by administering monorden to animals to induce multiple births, promote estrus synchronization, increase litter sizes, and increase conception rates.

BACKGROUND OF THE INVENTION

Monorden, 5-Chloro-6-(7,8-epoxy-10-hydroxy-2-oxo-3,5-undecadienyl)-$\beta$-resorcylic acid $\mu$-lactone, also known as radicicol, is an antibiotic substance isolated from several microorganisms including *Monosporium bonarden:* Delmotte, Delmotte-Plaquee, Nature 171, 344 (1953). The structural formula, physical, chemical, and other properties are given in the Merck Index, ninth edition, page 811, compound 6089.

The success and profit for animal breeders raising cattle, swine, sheep, goats, horses, mink, rats, mice, and many other animals depends largely upon the ability to produce large numbers of viable offspring. It is, therefore, desirable to increase the conception rate by insuring that each female is impregnated as often as possible and increase the birth rate and litter sizes by inducing multiple births from each impregnation. It is also important to promote estrus synchronization to control when offspring will be born. In the natural method, allowing two animals to mate, the female may fail to become pregnant up to 50% or more of the time and multiple births may be rare or litters may be smaller than desirable. It has been estimated that dairy farmers lose 10% of their total income because cattle fail to become impregnated on the first mating. Additionally, offspring are generally born at various times throughout the year instead of at a specific period controlled by the breeder.

Various methods have been developed to overcome these problems. Artifical insemination can improve the conception rate somewhat but generally does not increase the number of births per conception. Subsequently, methods to increase the success of artificial insemination were developed. For example, U.S. Pat. No. 4,119,089 discloses a method for predicting ovulation and therefor the best time for artifical insemination by monitoring volatile sulfur compounds in the animal's breath. These methods, however, have not been wholly successful particularly where animals that for whatever reasons are very difficult to impregnate or hold their breath.

Methods for increasing fertility in animals by stimulating and controlling ovulation have increased the conception rate. Treating animals with progesterone and other hormonal compounds can significantly increase the conception rate, but the high cost of hormonal products and the adverse side effects have prevented their widespread use. For example, U.S. Pat. Nos. 3,830,907 and 3,565,991 disclose using nortesterone compounds to control ovulation and estrus. Numerous patents, e.g. U.S. Pat. Nos. 2,379,832, 2,232,438, and 2,324,185, have related to progesterone which has been used to control habitual abortion and suppress or synchronize estrus. These compounds, however, are often expensive, difficult to handle, and have adverse side effects such as estrogenic-like changes in body weight, uterine weight, etc. in the animal.

Other compounds have also been used to increase fertility by controlling and stimulating ovulation. U.S. Pat. No. 4,283,419 discloses administering tris-(2-ethoxy-ammonium-orthocresoxy) acetate and U.S. Pat. No. 3,463,860 discloses administering para-hydroxybenzoic acid esters to increase fertility in animals. Japanese Patent No. 58043725 discloses feeding argenine and lysine to cattle to increase birth rate from approximately 50% to 83.3%. These compounds, however, generally have estrogen-type side effects chararacteristic of the analogous hormonal compounds.

An inexpensive and effective method is, therefore, needed which can increase fertility in animals by increasing the conception rate, inducing multiple births, increasing litter sizes, and promoting estrus syncronization without producing the adverse side effects characteristic of prior methods.

SUMMARY OF THE INVENTION

It is, therefore, an object of the present invention to increase fertility in animals.

It is another object of the present invention to increase the conception rate in animals.

It is another object of the present invention to increase the incidence of multiple births in animals.

It is another object of the present invention to increase litter sizes in animals.

It is another object of the present invention to promote estrus syncronization in animals.

It is another object of the present invention to control the ovulation cycle in animals.

It is a further object of the present invention to stimulate ovulation in animals.

These and other objects are achieved by the new use of a known compound, monorden. The objects are achieved by administering a fertility increasing amount of the active compound, monorden, to the animals. Monorden, administered in the proper dosage, has several desirable and beneficial effects; the conception rate is increased thereby optimizing the number of offspring produced, the incidence of multiple births is increased thereby producing more offspring per pregnancy, the litter size is increased thereby producing more offspring per pregnancy, and the estrus cycle is synchronized allowing the breeder to control when offspring will be born. Monorden lacks the undesirable estrogenic activity characteristic of some previous compounds but exhibits the beneficial progesterone-like activity characteristic of prior art compounds. The females treated with monorden according to the present invention had significantly more corpora lutea and the mean ovarian weight was significantly greater when compared to that of controls. No significant differences were observed in uterine weight, body weight, or weight gains for monorden-treated females thus indicating the lack of a general effect by Monorden on the endocrine system.

In the preferred embodiment, 0.5–1.0 mg/kg of body weight/day of monorden was injected subcutaneously to promote estrus synchronization and stimulate ovulation thereby increasing the conception rate, increasing incidence of multiple births, and increasing the litter size.

As used herein, the term monorden includes the compound and its pharmaceutically acceptable salts.

Other objects, advantages, and novel features of the present invention will become apparent from the following detailed description of the invention.

DETAILED DESCRIPTION OF THE INVENTION

Monorden is administered to animals to increase fertility and synchronize the estrus cycle by controlling and stimulating ovulation. Monorden administered in the proper dosages helps to insure conception and increase productivity by inducing multiple births and increasing litter sizes. Monorden also synchronizes the estrus cycle thereby permitting many young to be born at one time rather than spread out over a period of time. Additionally, ovulation control and stimulation are useful for work with transgenic animals.

The amount of monorden administered may vary depending upon the particular type of animal, the maturity of the animal, and the size of the animal. Generally, monorden is administered to the animals and the dosage from 0.1–5 mg/kg of body weight/day, preferably from 0.2–2 mg/kg of body weight/day, and most preferably from 0.5–1 mg/kg of body weight/day.

Monorden can be administered by any suitable method including administering monorden to the animals in injections, tablets, suspensions, implants, solutions, emulsions, capsules, powders, syrups, water compositions, or feed compositions. Injections, feed compositions, and implants are preferred with injections being most preferred. Monorden is preferably administered parenterally. Such administration may be by intravenous or intramuscular injection, intraperitoneal injection, or subcutaneous implant. Monorden can also be administered orally, preferably as a feed additive in an acceptable feed composition.

Animals treatable with monorden include humans, cattle, swine, sheep, goats, oxen, horses, mice, rats, mink, and other animals.

Monorden can be administered to the animals with any biocompatible and monorden compatable carrier such as various vehicles, adjuvants, additives, and diluents to achieve a formulation or composition usable as a dosage form. For example, injectable formulations of Monorden are prepared using "Cornell buffer" which consists of isotonic saline containing 0.025 $NaHCO_3$ and 0.25 molar $Na_2CO_3$. Formulations of Monorden are prepared every four days and kept at 4° C. until used. The saline/buffer vehicle is prepared in bulk and sterilized by filtration. Monorden is added aseptically to the buffer vehicle in amounts sufficient to supply from about 0.1–5 mg/kg of body weight/day to the animal when injected. Preferably, monorden is added to a SSV vehicle (an aqueous NaCL (0.9%), polysorbate-80 (0.4%), CMC (0.5%), and benzyl alcohol (0.9%) mixture) in amounts sufficient to supply from about 0.1–5 mg/kg of body weight/day, depending upon the size of the animal, and injected up to fourteen days prior to conception.

Aqueous vehicles such as water having no nonvolatile pyrogens, sterile water, and bacteriostatic water are also suitable to form injectable monorden formulations. In addition to these forms of water, several other aqueous vehicles can be used. These include isotonic injection formulations that can be sterilized such as sodium chloride, Ringer's, dextrose, dextrose and sodium chloride, and lactated Ringer's. Addition of water-miscible solvents, such as methanol, ethanol, or propylene glycol generally increases solubility and stability of monorden in these vehicles.

Nonaqueous vehicles such as cottonseed oil or peanut oil and esters such as isopropyl myristate may also be used as solvent systems for monorden formulations. Additionally various additives which enhance the stability, sterility, and isotonicity of the composition including antimicrobial preservatives, antioxidants, chelating agents, and buffers can be added. Any vehicle, diluetent, or additive used would, however, have to be compatible with monorden.

Monorden can be administered to the animal in the form of a slow-release subcutaneous implant which is inserted beneath the skin of the animal, preferably on the ear. The implant can take the form of a pellet which slowly dissolves after being implanted in the animal or a biocompatible and Monorden compatible delivery module well known to those skilled in the art. Such well known dosage forms are designed such that the active ingredients are slowly released over a period of several days to several weeks. The implant is designed to deliver from about 0.1–5 mg/kg of body weight/day to the animal.

Monorden can be administered oraly to the animal. For example, monorden can be blended with ordinary feed compositions or added to drinking water in amounts sufficient to increase the animal's fertility or control estrus synchronization in the animal. When monorden is to be administered in feeds, an animal feed composition may be prepared containing the usual nutritionally-balanced feed containing quantities of carbohydrates, proteins, vitamins and minerals, together with monorden in accordance with the present invention. Some of the usual dietary elements included in animal feed compositions are grains, such as ground grain and grain byproducts, animal protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with cattle includes alfalfa hay and ground corncobs together with supplementary vitamins and vitamin-containing substances if desired. Monorden is admixed with the feed in amounts sufficient to supply from about 0.1–5 mg/kg of body weight/day to the animal.

The invention having been generally described, the following examples are given as particular embodiments of the invention and to demonstrate the practice and advantages thereof. It is understood that the examples are given by way of illustration and are not intended to limit the specification or the claims to follow in any manner.

EXPERIMENT I

Production of Monorden

To prepare a primary inoculum for monorden production, mycelia of *Diheterospora chlamydosporia* (ATCC 20537) were scraped from a seven-day nutrient agar slant and suspended in 5 ml of sterile distilled water. This suspension was used to inoculate flasks of nutrient broth which were shaken (300 rpm) at 28° C. for six days.

Secondary stage seed cultures were prepared in two, 16-liter Microgen fermentors (New Brunswick Scientific Co.). A 5% (vol/vol) inoculum was transferred to ten liters of nutrient broth which were agitated (550–650 rpm), aerated (10 liters/minute), and held at 28° C. under back pressure (3 lbs/in$^2$) for four days.

Compound K-67 (Hodag Chemical) was used as an antifoam agent at a level of 0.1%.

A 4% (vol/vol) seed was then used to inoculate two pilot plant S-units (S-10 and S-11) each containing 227 liters of nutrient broth. Temperature (28° C.), agitation rate (250 rpm), aeration (5 cfm), and back pressure (5 lbs/in ) were maintained for six days.

Fermentor samples were collected daily to monitor cell growth and monorden production. Prior to filtration, Super-Cel filter aid (5% wt/vol) was added to 100 ml of culture and the fungal mycelia were separated from the culture broth. The filter cake as slurried in methylene chloride for 30 minutes, refiltered, and the extracts were examined spectrophotometrically. In addition, extracts were examined for the presence of monorden by thin layer chromatography (TLC). Samples (20 μl were spotted on silica gel sheets (Eastman Chromagram) containing fluorescent indicator, and the chromatograms were developed in $CHCl_3$-$CH_3OH$ (98:2). Fluorescent spots were detected by exposing the TLC sheets to UV light prior to iodine vapor exposure. Also, biological activity of the extracts was assessed by agar disc diffusion plate tests for antimicrobial activity against two indicator organisms, *Candida albicans* and *Saccharomyces cerevisiae*. The results are summarized:

|  | $A_{265}$ | Rf in $CHCl_3$—$CH_3OH$ (98:2) | Antimicrobial Activity |
|---|---|---|---|
| Monorden Standard (1 mg/ml) | 68.0 | 0.23 | + |
| Mycelial Extract (S-10) | 33.6 | 0.22 | + |
| Mycelial Extract (S-11) | 31.2 | 0.22 | + |

Referring to the summary, methylene chloride extracts of fungal mycelia on day six of the fermentation exhibited ultraviolet spectra characteristic of monorden. Peak absorbance occurred at 265 nm due to the aromatic ring structure. When examined by TLC, extracts were found to contain a major component with mobility similar to that of monorden standard. The anticipated biological activity of monorden was confirmed since extracts were found to possess antifungal activity against *Candida albicans* and *Saccharomyces cerevisiae* in the agar disc diffusion assay.

EXPERIMENT II

In vivo Monorden tests

Immature female rats of a Sprague-Dawley derived strain (King Animal Laboratories, Oregon, Wisconsin) weighing 72 to 80 g, were obtained and treatment initiated at 30 days of age. Each animal was given a unique identification number and was marked by an ear punch method. Due to the age restrictions of the protocol, the animals were not acclimated in the test facility prior to treatment. The rats were assigned at random to treatment groups consisting of 10 animals per group and were weighed to the nearest gram. The rats were group housed (five/cage) in stainless steel wire cages and in an air-conditioned room at 72° F.±3°, with 50±20 percent relative humidity, and a 12-hour light and 12-hour dark cycle. The animals were maintained on Purina Lab Chow and tap water ad libitum. The test material was administered by subcutaneous injection in a solution of Steroid Suspending Vehicle (SSV) (an aqueous NaCL (0.9%), polysorbate-80 (0.4%), CMC (0.5%), and benzyl alcohol (0.9%) mixture) once daily for 14 days at the specified doses as shown:

| Group | Treatment | Daily Dose |
|---|---|---|
| 1 | SSV | 0.2 mg |
| 2 | Monorden | 0.5 mg |
| 3 | Monorden | 1.0 mg |
| 4 | Monorden | 2.0 mg |
| 5 | Zeranol | 0.5 mg |
| 6 | Zeranol | 1.0 mg |
| 7 | Zeranol | 2.0 mg |

The animals were sacrificed by $CO_2$ euthanasia on the day following the last day of treatment (Day 15) and final body weight was recorded to the nearest gram. The following tissues were excised, dissected free of extraneous connective tissue and weighed to the nearest 0.1 mg: ovaries, uterus, adrenals, thyroid and pituitary. The ovaries were examined in transmitted light and the number of corpora lutea (CL) were recorded, or the presence of follicles in the absence of CL. The thymus, spleen and left kidney were dissected and weighed to the nearest milligram. The liver was dissected and weighed to the nearest 0.1 g.

Means and standard errors of the mean (SEM) were calculated for body and organ weight for each treatment group. The weights of the spleen, left kidney and liver also were normalized to body weight (mg or g/100 g final body weight). The data was analyzed by analysis of variance, and significant differences between the control and treatment groups were determined by the Dunnett's multiple comparison test. Results of this study are summarized in Table 1.

Referring to Table 1, the control zeranol significantly decreased the body weight gain and significantly increased the uterus weight compared to the SSV control. There was, however, no change in the body weight or uterus weight for the monorden treated animals thereby indicating that monorden lacks estrogenic properties. Monorden, however, when compared to the SSV and controls, significantly increased the ovarian weight and the number of corpora lutea produced by the monorden treated animals. Additionally, the other endocrine organs of the monorden treated animals, adrenals, thymus, thyroid, pituitary, spleen, kidney, and liver, showed no significant changes compared to those of the controls. Monorden, therefore, lacks estrogenic properties, increases fertility as indicated by the increased ovarian weight and number of corpora lutea, and has no side effects on the general endocrine system.

Obviously many modifications and variations of the present invention are possible in light of the above teachings. It is, therefore, to be understood that within the scope of the appended claims the invention may be practiced otherwise than as specifically described.

TABLE I

| Female Rat General Endocrine Screen ||||||||
|---|---|---|---|---|---|---|---|
| Body Weights || | Ovarian | No. of | | | |
| Initial | Final | Body | Weight | Corpora | Uterus | Adrenals | Thymus |
| g | g | Weight Gains | mg | Lutea | mg | mg | mg |

TABLE I-continued

Female Rat General Endocrine Screen

| | | | | | | | | | |
|---|---|---|---|---|---|---|---|---|---|
| Control | | | | | | | | | |
| Mean | 76 | 139 | 63 | 82 | 56.6 | 6 | 270.6 | 53.6 | 377 |
| SE | 0.6 | 1.5 | 1.7 | 2.5 | 2.51 | 0.8 | 16.84 | 1.41 | 19.8 |
| 0.5 mg Monorden | | | | | | | | | |
| Mean | 76 | 140 | 64 | 85 | 60.4 | $11.0^{(b),(c)}$ | 288.7 | 55.0 | 390 |
| SE | 0.6 | 2.2 | 1.9 | 2.4 | 3.96 | 1.6 | 18.22 | 1.60 | 16.4 |
| 1.0 mg Monorden | | | | | | | | | |
| Mean | 76 | 141 | 65 | 86 | $67.2^{(a)}$ | $12.0^{(b),(c)}$ | 281.82 | 57.9 | 425 |
| SE | 0.6 | 1.5 | 1.6 | 2.4 | 3.36 | 1.1 | 17.56 | 2.11 | 17.2 |
| 2.0 mg Monorden | | | | | | | | | |
| Mean | 75 | 135 | 61 | 81 | 55.2 | 8 | 272.6 | 55.1 | 392 |
| SE | 0.5 | 1.6 | 1.5 | 1.9 | 3.01 | 0.8 | 25.54 | 2.24 | 15.7 |
| 0.5 mg Zeranol | | | | | | | | | |
| Mean | 76 | $114.0^{(b)}$ | $38.0^{(b)}$ | $51.0^{(b)}$ | $23.4^{(b),(c)}$ | $1.0^{(b),(c)}$ | 317.8 | $42.3^{(b)}$ | $154^{(b),(c)}$ |
| SE | 0.6 | 1.4 | 1.5 | 2.1 | 1.82 | 0.5 | 2.46 | 1.43 | 6.1 |
| 1.0 mg Zeranol | | | | | | | | | |
| Mean | 75 | $113^{(b)}$ | $37^{(b)}$ | $50^{(b)}$ | $17.7^{(b),(c)}$ | $0^{(b),(c)}$ | $382.0^{(b)}$ | 47.2 | $146^{(b),(c)}$ |
| SE | 0.6 | 2.0 | 2.1 | 2.8 | 0.69 | 0.1 | 17.81 | 1.73 | 7.7 |
| 2.0 mg Zeranol | | | | | | | | | |
| Mean | 75 | $111^{(b)}$ | $36^{(b)}$ | $48^{(b)}$ | $20.6^{(b),(c)}$ | $1^{(b),(c)}$ | $343.0^{(a)}$ | $42.4^{(b)}$ | $125^{(b),(c)}$ |
| SE | 0.5 | 1.7 | 1.8 | 2.5 | 1.90 | 0.4 | 17.56 | 1.79 | 8.9 |

| | Thyroid mg | Pit mg | Spleen mg/100 g | | L Kidney mg/100 g | | Liver mg/100 g | |
|---|---|---|---|---|---|---|---|---|
| | | | mg | Body Wt | mg | Body Wt | g | Body Wt |
| Control | | | | | | | | |
| Mean | 21.0 | 13.4 | 543 | 391 | 772 | 556 | 9.0 | 6.5 |
| SE | 1.00 | 0.71 | 20.8 | 16.3 | 20.6 | 15.1 | 0.20 | 0.13 |
| 0.5 mg Monorden | | | | | | | | |
| Mean | 23.0 | 15.5 | 565 | 404 | 755 | 541 | 8.6 | 6.2 |
| SE | 1.06 | 0.91 | 12.5 | 11.3 | 15.5 | 12.6 | 0.28 | 0.13 |
| 1.0 mg Monorden | | | | | | | | |
| Mean | 22.2 | 14.3 | 583 | 414 | 839 | 596 | 8.8 | 6.2 |
| SE | 0.99 | 0.78 | 21.1 | 13.8 | 22.7 | 12.3 | 0.16 | 0.09 |
| 2.0 mg Monorden | | | | | | | | |
| Mean | 20.7 | 11.7 | 584 | 431 | 805 | 594 | 8.5 | 6.3 |
| SE | 0.79 | 0.66 | 25.9 | 18.3 | 19.2 | 13.4 | 0.32 | 0.19 |
| 0.5 mg Zeranol | | | | | | | | |
| Mean | $12.4^{(b),(c)}$ | $10.7^{(a)}$ | $390^{(b),(c)}$ | $342^{(a)}$ | 738 | $646^{(b)}$ | $7.3^{(b),(c)}$ | 6.4 |
| SE | 0.59 | 0.52 | 13.2 | 10.2 | 26.4 | 20.5 | 0.26 | 0.18 |
| 1.0 mg Zeranol | | | | | | | | |
| Mean | $12^{(b),(c)}$ | 11.6 | $379^{(b),(c)}$ | $337^{(a)}$ | 712 | $633^{(b)}$ | $7.4^{(b),(c)}$ | 6.5 |
| SE | 0.75 | 0.37 | 7.0 | 8.9 | 17.5 | 10.6 | 0.23 | 0.14 |
| 2.0 mg Zeranol | | | | | | | | |
| Mean | $14.0^{(b),(c)}$ | $10.8^{(a)}$ | $376^{(b),(c)}$ | $339^{(a)}$ | $648^{(b)}$ | 586 | $7.2^{(b),(c)}$ | 6.5 |
| SE | 0.74 | 0.30 | 9.2 | 0.3 | 12.5 | 16.5 | 0.28 | 0.18 |

Where SE is the standard error and the superscripts $^{(a)-(d)}$ are defined as follows: $^{(a)}$ means significantly different from control ($p \leq .05$), $^{(b)}$ means significantly different from control ($p \leq .01$), $^{(c)}$ means significantly different from control ($p \leq .01$) using covariate analysis, and $^{(d)}$ means significantly different from control ($p \leq .05$) using covariate analysis.

I claim:

1. A method for increasing fertility in female animals which comprises the step of administering a fertility increasing amount of monorden to said animal in need thereof thereby increasing the conception rate, incidence of multiple ovulation, and litter sizes.

2. The method of claim 1 wherein the amount of monorden administered is from about 0.1-5 mg/kg of body weight/day.

3. The method of claim 1 wherein said animals are humans, cattle, horses, swine, sheep, goats, mink, mice, and rats.

4. The method of claim 1 wherein monorden is administered orally, said oral method selected from the group consisting of administering monorden to said animals in tablets, suspensions, implants, solutions, emulsions, capsules, powders, syrups, drinking water compositions, and feed compositions.

5. The method of claim 1 wherein said monorden is administered in a feed composition, said feed composition further comprising:

a nutritionally balanced feed; and a fertility increasing amount of monorden admixed with said feed.

6. The method of claim 1 wherein said monorden is administered by injecting a monorden formulation, said formulation further comprising:

a biocompatible and monodren compatable vehicle; and a fertility-increasing amount of monorden admixed with said vehicle.

7. The method of claim 6 wherein said vehicle is an aqueous NaCL (0.9), polysorbate-80 (0.4%), CMC (0.5%), and benzyl alcohol (0.9%) mixture.

8. The method of claim 1 wherein said monorden is administered using an implant, said implant further comprising:

a biocompatible and monodren compatable implant material; and a fertility-increasing amount of monorden admixed with said implant material.

9. A method for estrus synchronization in female animals which comprises the step of administering a estrus synchronizing amount of monorden to said animals in need thereof.

10. The method of claim 9 wherein the amount of monorden administered is from about 0.1–5 mg/kg of body weight/day.

11. The method of claim 9 wherein said animals are humans, cattle, horses, swine, sheep, goats, mink, mice, and rats.

12. The method of claim 9 wherein monorden is administered orally, said oral method selected from the group consisting of administering monorden to said animals in tablets, suspensions, implants, solutions, emulsions, capsules, powders, syrups, drinking water compositions, and feed compositions.

13. The method of claim 9 wherein said monorden is administered in a feed composition, said feed composition further comprising:

a nutritionally balanced feed; and an estrus synchronizing amount of monorden admixed with said feed.

14. The method of claim 9 wherein said monorden is administered by injecting a monorden formulation, said formulation further comprising:

a biocompatible and monodren compatable vehicle; and an estrus synchronizing amount of monorden admixed with said vehicle.

15. The method of claim 14 wherein said vehicle is an aqueous NaCL (0.9%), polysorbate-80 (0.4%), CMC (0.5%), and benzyl alcohol (0.9%) mixture.

16. The method of claim 9 wherein said monorden is administered using an implant, said implant further comprising:

a biocompatible and monodren compatable implant material; and an estrus synchronizing amount of monorden admixed with said implant material.

* * * * *

UNITED STATES PATENT AND TRADEMARK OFFICE
CERTIFICATE OF CORRECTION

PATENT NO. : 4,707,492

DATED : November 17, 1987

INVENTOR(S) : Paula Myers-Keith

It is certified that error appears in the above-identified patent and that said Letters Patent are hereby corrected as shown below:

Column 2, lines 15 & 16, "syncronization" should read -- synchronization --

Column 2, line 30, "syncronization" should read -- synchronization --

Column 3, line 37, "biocompatable" should read -- biocompatible --

Column 3, line 37, "compatable" should read -- compatible --

Column 4, line 6, "diluetent" should read -- diluent --

Column 4, line 20, "oraly" should read - orally --

Column 5, lines 6 & 7, "(5 lbs/in)" should read -- (5 lbs/in$^2$) --

Column 8, Claim 6, line 4, "monodren" should read -- monorden --

Column 8, Claim 6, line 4, "compatable" should read -- compatible --

Column 8, Claim 7, line 2, "(0.9)"should read -- (0.9%) --

Column 8, Claim 8, line 4, "monodren" should read -- monorden --

Column 8, Claim 8, line 4, "compatable" should read -- compatible --

Column 9, Claim 9, line 2, "a" should read -- an --

Column 10, Claim 14, line 4, "monodren" should read -- monorden --

Column 10, Claim 14, line 4, "compatable" should read -- compatible --

Column 10, Claim 16, line 4, "monodren" should read -- monorden --

UNITED STATES PATENT AND TRADEMARK OFFICE
CERTIFICATE OF CORRECTION

PATENT NO. : 4,707,492
DATED : November 17, 1987
INVENTOR(S) : Paula Myers-Keith It is certified that error appears in the above-identified patent and that said Letters Patent is hereby corrected as shown below:

Column 10, Claim 16, line 4, "compatable" should read -- compatible --.

Signed and Sealed this

Seventh Day of June, 1988

Attest:

*Attesting Officer*

DONALD J. QUIGG

*Commissioner of Patents and Trademarks*